United States Patent [19]

Farin et al.

[11] Patent Number: 4,658,815
[45] Date of Patent: Apr. 21, 1987

[54] HIGH-FREQUENCY ELECTROSURGICAL UNIT WITH TIMED SAFETY SHUT DOWN INTERLOCK

[75] Inventors: Günter Farin; Peter Pütz, both of Tuebingen, Fed. Rep. of Germany

[73] Assignee: Erbe Elektromedizin GmbH, Tuebingen, Fed. Rep. of Germany

[21] Appl. No.: 819,468

[22] Filed: Jan. 15, 1986

Related U.S. Application Data

[63] Continuation of Ser. No. 514,473, Jul. 18, 1983, abandoned.

[30] Foreign Application Priority Data

Jul. 28, 1982 [DE] Fed. Rep. of Germany ....... 3228136

[51] Int. Cl.⁴ .............................................. A61B 17/36
[52] U.S. Cl. ........................... 128/303.14; 128/303.17; 128/419 R
[58] Field of Search ...................... 128/303.13, 303.14, 128/303.17, 419 R; 364/707

[56] References Cited

U.S. PATENT DOCUMENTS

| | | | |
|---|---|---|---|
| 3,812,858 | 5/1974 | Oringer | 128/303.14 |
| 3,952,748 | 4/1976 | Kaliner et al. | 128/303.14 |
| 3,955,185 | 5/1976 | Nishimura | 364/707 |
| 4,038,984 | 8/1977 | Sittner | 128/303.14 |
| 4,051,855 | 10/1977 | Schneiderman | 128/303.14 |
| 4,074,719 | 2/1978 | Samm | 128/303.17 |
| 4,191,188 | 3/1980 | Belt et al. | 128/303.13 |
| 4,338,940 | 7/1982 | Ikunu | 128/303.17 |

Primary Examiner—Edward M. Coven
Attorney, Agent, or Firm—Frishauf, Holtz, Goodman & Woodward

[57] ABSTRACT

A supplementary acoustic warning signal is provided for a high-frequency electrosurgical unit which sounds only after the lapse of an interval set by a first delay circuit shows that one of the high-frequency generators in the unit remains active longer than what, on the average, is normal. A second delay circuit is provided to assure shut-off of the high-frequency generators if at least one of the high-frequency generators remains active without interruption longer by an interval set by a second delay circuit beyond the lapse of an interval of the interval set by the first delay circuit. The supplementary acoustic signal thus sounds before the second delay circuit shuts off the high-frequency generators. The intervals determined by each of the delay circuits are adjustable. The output signal of the second delay circuit which activates the shut-off relays is maintained until a switch is operated to reset the system, so that the malfunction which has led to shut-down will be dealt with before the unit is used again.

15 Claims, 2 Drawing Figures

HIGH-FREQUENCY ELECTROSURGICAL UNIT WITH TIMED SAFETY SHUT DOWN INTERLOCK

This application is a continuation of application Ser. No. 514,473, filed July 18, 1983, now abandoned.

This invention concerns a high-frequency electrosurgical unit for cutting and coagulating biological tissues in which one or more high-frequency generators are controllable by finger switches, foot switches or automatic switch systems and when there are two or more of them, can be controlled simultaneously or independently from each other, and particularly units of that type containing means for producing visible and audible signals while one or more of the high-frequency generators are in operation.

The high-frequency generators of high-frequency electrosurgical units already known can be activated simultaneously or independently of each other for any length of interval and as often as desired by finger switches, of which switches are automatic switching devices.

The high frequency electrosurgical units are dangerous in activated condition, since each contact of the patient or of operating personnel with the active electrode can produce burns and this holds, for example, even for the neutral electrode in the case of apparatus with floating output. Finger switches or foot switches which activate the high-frequency generators only while the surgeon or his assistant presses the corresponding switch and immediately switch off the high-frequency generators when the switch is no longer pressed are used in high-frequency electrosurgical units now in use on account of the danger just mentioned. In addition, known high-frequency electrosurgical units are equipped with optical and acoustic signal devices which are activated at the same time as the high-frequency generators. By this means the surgeon and other personnel present are intended to be made aware of the danger even during intended activation of the high-frequency generators.

It has been found in practical application of the known high-frequency electrosurgical units that the optical and acoustical signals do not provide sufficient safety against burns or injuries to patients or personnel. The optical signal devices of known high-frequency electrosurgical units are always disposed on the front panel of the units, which as a rule cannot continuously be observed either by the surgeon or by other attending personnel during an operation. The high-frequency electrosurgical unit is often placed as far as possible from the operating table, since freedom of movement must be assured for the surgeon. The acoustic signal that is activated simultaneously with the high-frequency generators is regarded as disturbing by many surgeons, because it distracts them from their concentration, so that this signal is either set very low or completely shut off. On the other hand there are surgeons who become so used to the acoustic signal that they lose all awareness of it. A clearly significant signal would be particularly important when the high-frequency generators of the high-frequency electrosurgical units are unintentionally activated. Unintentional activation of the high-frequency generators can result from unintentional actuation of the finger switch or foot switch, or of its circuit by failures in the switches or in the cables or plug connectors thereof. Failures in the electronics within the high-frequency electrosurgical units can also activate the high-frequency generator. This holds also for automatic switch-on equipment.

Accidents have also come to light in which electrically conducting liquids, such as blood, physiological salt solutions, urine or fruit juice for example, have flowed into the finger switches set in hand controls, as a result of which the high-frequency generators have been unintentionally activated.

In the case of unintentional activation of the high-frequency generators, particularly as the result of technical errors or failures, the presence of the known optical and acoustical signals alone is not sufficient, in some cases, for the resulting danger to be recognized in time, and, in particular, to be reacted to sufficiently fast and correctly. This applies, for example, to endoscopic operations. If a high-frequency electrosurgical unit is unintentionally activated as the result of a technical failure during a transurethral resection, the resection loop used in such an operation could cut right through the urinary bladder before the surgeon recognizes the danger and has made the correct reaction thereto.

SUMMARY OF THE INVENTION

It is an object of the present invention to provide a high-frequency electrosurgical unit in which unintended activation resulting from causes like those mentioned above do not lead to any threat to the safety of the patient or the user, or at least greatly reduce the danger.

Briefly, a supplementary signal system is provided which is triggered by a first delay circuit only when a high-frequency generator has remained activated for more than a predetermined time interval and a second delay circuit is provided for switching off the high-frequency generators by a cut-off relay when a high-frequency generator has remained activated longer than the delay period of the first delay circuit, so that the supplementary acoustic signal is provided as a warning before the second delay circuit shuts off the high-frequency generator. The additional acoustic signal provided by the present invention which is distinct from the known acoustic signals activated simultaneously with the high-frequency generator and appears only after at least one of the usually more than one high-frequency generators of a high-frequency electrosurgical unit has remained in operation longer than what is on the average usual, is produced by means of a delay circuit that is definitively adjustable to an appropriate setting. Furthermore, the high frequency electrosurgical unit according to the invention is equipped with a shut-off relay that is activated by another adjustable delay circuit which assures the automatic shutting off of the high-frequency generators after the lapse of the sum of the two delay intervals and also keeps them shut off thereafter until a reset switch is actuated on the high-frequency electrosurgical unit and thereby releases the shut-off relay and enables the reactivation of the high-frequency generator.

THE DRAWINGS

The invention is further described by way of illustrative example with reference to the annexed drawings, in which:

FIG. 1 is a block circuit diagram of a high-frequency electrosurgical unit according to the invention, and FIG. 2 is a circuit diagram of the two delay circuits of the embodiment shown in FIG. 1.

DESCRIPTION OF THE PREFERRED EMBODIMENT

Figure 1:
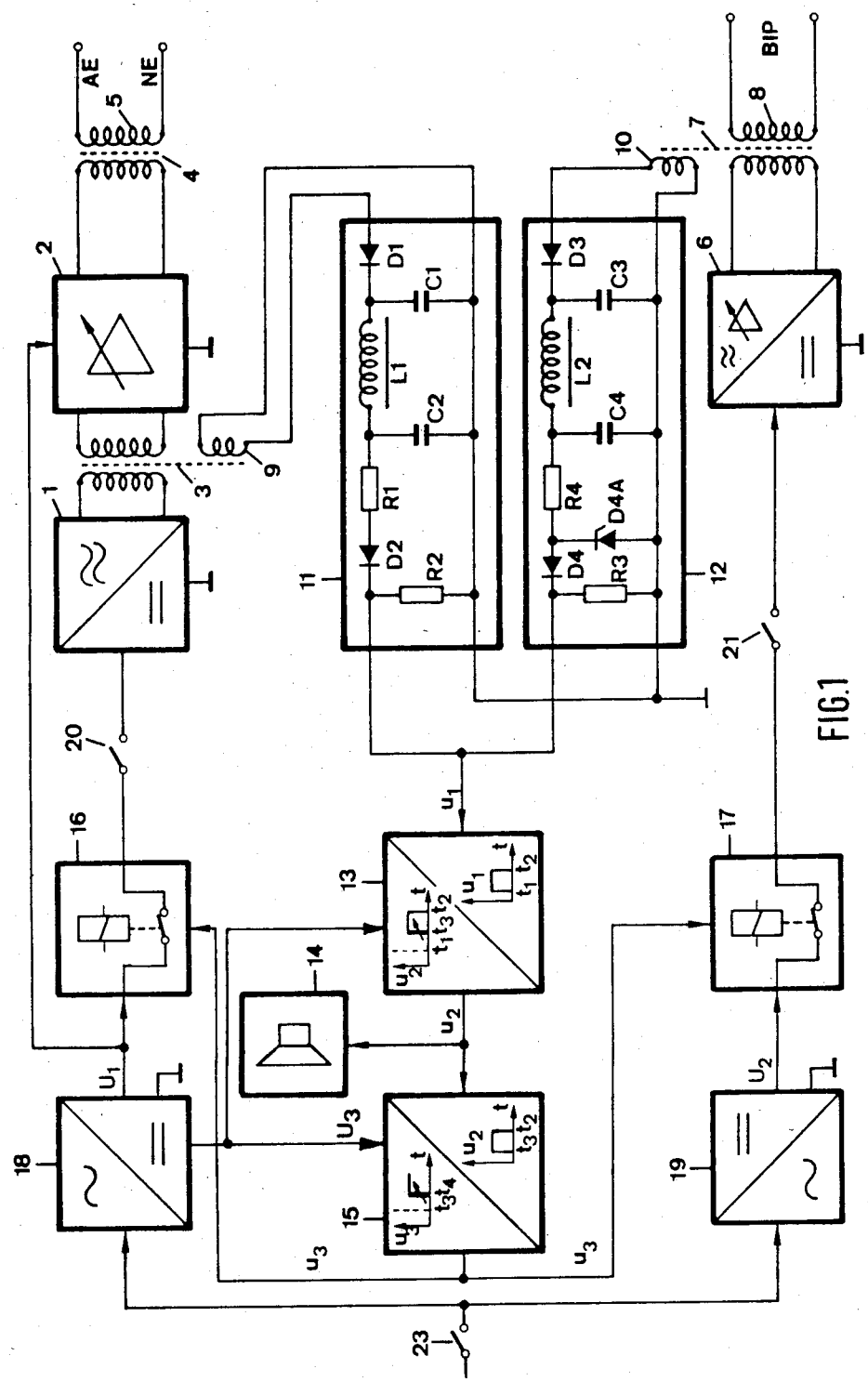

The high-frequency electrosurgical unit of FIG. 1 contains two high-frequency generators 1 and 6. A power amplifier 2 is coupled by a transformer 3 to the oscillator of the high-frequency generator 1. The output of the power amplifier 2 can be adjusted in level over a wide range (e.g. from 2 watts to 400 watts). Another transformer 4 is connected to the output of the power amplifier 2 which provides the potential isolation necessary for high-frequency electrosurgical unit between the low-frequency supply voltage $U_1$ and the circuit that passes through the patient. The first high-frequency generator 1 is a conventional high-frequency oscillator, with its frequency controlled by an external circuit or a stabilizing element such as a quartz crystal.

An active electrode AE and a neutral electrode NE are shown in FIG. 1 connected to the secondary winding 5 of the transformer 4, these electrodes representing any of the well-known electrode arrangements used with high-frequency surgical apparatus.

The second high-frequency generator 6 shown in FIG. 1 is a self-excited HF generator including its own output adjustment by which its output power can be set at any value within a wide range, (e.g. from 2 to 50 watts). The output of the high-frequency generator 6, like that of the power amplifier 2 of the high-frequency generator 1 is equipped with an output transformer 7. The secondary winding of this transformer 7 is designed, for example, for bipolar coagulation electrodes designated BIP.

Windings 9 and 10 are respectively coupled to the high-frequency transformers 3 and 7 and have high-frequency voltages induced therein if and so long as the respective high-frequency generators 1 and 6 are active. These high-frequency alternating voltages are rectified in rectifiers 11 and 12 respectively by diodes $D_1$ and $D_3$ and filtered (smoothed) by capacitors $C_1$, $C_2$, $C_3$ and $C_4$ and inductances $L_1$ and $L_2$ as shown in FIG. 1.

The capacitors $C_1$ to $C_4$ and the inductances $L_1$ and $L_2$ have sufficiently great electrical values of capacitance and inductance respectively while filtering out not only the high H frequency but any lower modulation frequency, such as are used in high-frequency electrosurgical unit for producing coagulation (e.g. 20 kHz). The outputs of the two rectifiers 11 and 12 are brought together into a common circuit through the respective diodes $D_2$ and $D_4$. A voltage-limiting diode $D_{4A}$ is connected so as to limit the output voltage of the rectifier 12. At the output of the rectifiers 11 and/or 12 a d.c. voltage level is produced so long as the respective high-frequency generators 1 and/or 6 is or are activated and that d.c. level produced by rectification is then supplied to a delay circuit 13. Resistances $R_2$ and $R_3$ are designed to discharge the respective capacitor pairs $C_1$, $C_2$ and $C_3$, $C_4$ sufficiently fast as the respective high-frequency generators are shut off.

Figure 2:
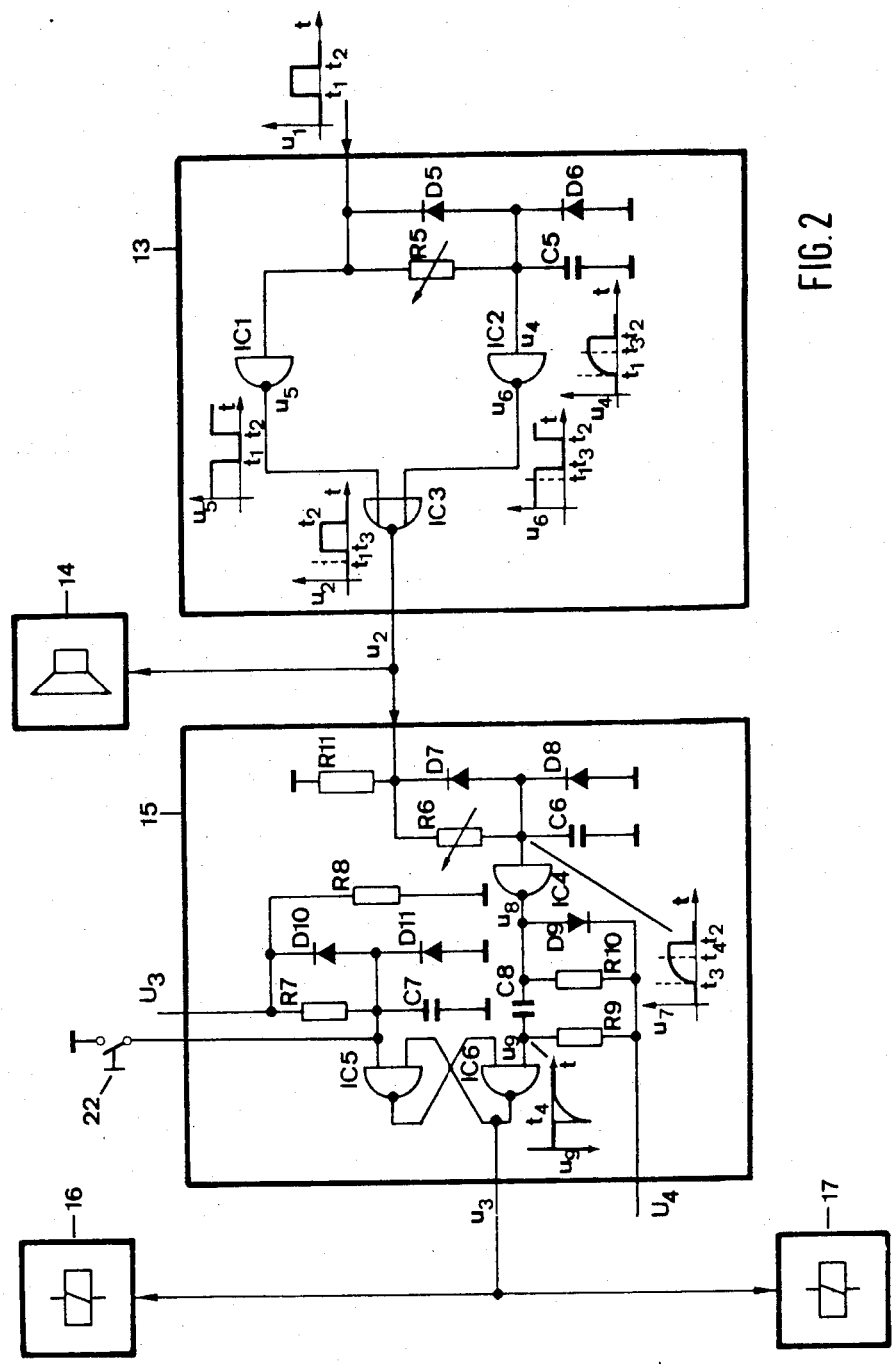

As soon as one of the two high-frequency generators 1 and 6 is switched on, there arises, with neglibible delay from the time constants of the components of the rectifiers 11 and 12, at the instant $t_1$ a d.c. voltage $u_1$ at the input of the delay circuit 13 which dies away again as soon as the respective high-frequency generators are shut off. The shut-off instant is designated $t_2$ in this context. The instant $t_1$ is thus the instant at which at least one of the high-frequency generators is switched on. The instant $t_2$ is the instant at which the last of all of the high-frequency generators that may have been operating is shut off. As soon as a voltage $u_1$ arises at the input of the delay circuit 13 at the instant $t_1$, the delay element (as shown in FIG. 2 and described below) in the delay circuit 13 becomes effective and after the delay interval $t_{13}=t_3-t_1$ which has been set, for example, at 3 seconds, delivers a voltage $u_2$ at the instant $t_3$ to the output of the delay circuit 13. The duration of the delay interval $t_{13}$ is adjustable. The output voltage $u_2$ is maintained until all high-frequency generators are shut off, which happens at the instant $t_2$. The delay interval $t_{13}=t_3-t_1$ can be set as required, so that according to the intended application of the high-frequency electrosurgical unit this delay interval $t_{13}$ will be greater than the normal switch-on duration of the high-frequency generators. Thus, at the output of the delay circuit 3 no voltage $u_2$ arises in normal operation and all following stages remain out of operation. If, however, as the result of operator error or a failure in the switch-on electronics or in the finger-operated or foot-operated switch, at least one of the high-frequency generators is activated longer than $t_{13}=t_3-t_1$, an output voltage $u_2$ arises at the instant $t_3$ at the output of the delay circuit 13, causing an acoustic signal to be emitted at once by triggering a signal device 14, making the surgeon aware of the fact that the normal switch-on interval has been exceeded. If the acoustics warning signal sounds even though the surgeon has already turned off the high-frequency generators, the surgeon or other attending personnel know at once that the high-frequency electrosurgical unit has malfunctioned and can deal with it correspondingly, for example turning off the supply of power to the equipment from the electrical supply lines. If this acoustic warning signal is disregarded or if no action is taken for reliably shutting down the high-frequency generator, a second delay circuit 15 becomes effective which will assure the shut-off of all high-frequency generators by their shut-off relays 16 and 17 after the further adjustable delay interval $t_{15}=t_4-t_3$.

The aggregate delay $t_a=t_4-t_1$ can be so set by suitable selection of the individual delay $t_{13}=t_3-t_1$ and $t_{15}=t_4-t_3$ that damage in case of error can be limited to a minimum.

A Zener diode is provided in the rectifier 12 which limits the output voltage $u_1$. This is necessary because the input coupling coil 10 of the rectifier 12 is coupled to the output transformer 7 of the high-frequency generator 6, where the voltage induced in the coil 10 depends both on the power adjustment of the high-frequency generator 6 and the loading of the coil 8. Limiting of the output voltage $u_1$ is not necessary in the rectifier 11, because the coupling coil 9 is coupled to the transformer 3, so that the voltage induced in the coil 9 is independent of the output power of the power amplifier 2 and of the loading of the secondary coil 5.

FIG. 2 shows an illustrative embodiment of both of the delay circuits 13 and 15. The input voltage $u_1$ is inverted in inverters $IC_1$ and $IC_2$, the input signal $U_4$ of $IC_2$ $\Delta$ being delayed by the time constant of a combination of an adjustable resistor $R_5$ and a capacitor $C_5$ for a time lapse $\Delta t_{13}=t_3-t_1$. In contrast thereto the inverted output signal $u_5$ produced by $IC_1$ appears undelayed at the inverter output. If $u_1$ is switched off at the instant $t_2$, then $IC_5$ immediately discharges via the diode $D_5$ and the resistances $R_2$ and $R_3$ (in FIG. 1), as the result of which the switch-off instant $t_2$ appears practically undelayed at the output of $IC_2$. A diode $D_6$ is provided to limit negative input voltage of $IC_2$.

The respective output voltages $u_5$ and $u_6$ of the inverters $IC_1$ and $IC_2$ are supplied to a NOR logic element $IC_3$ at the output of which the voltage $u_2$ appears only when $t_2$ takes longer to appear than $t_3$, at which time both input voltages $u_5 = u_6 = 0$.

The high-frequency generator can be activated as often as desired without appearance of the output voltage $u_2$ at the output of $IC_3$. If the high-frequency generators are not activated without interruption for a duration longer than $\Delta t_{13} = t_3 - t_1$, that is, so long as $t_2 - t_1 < t_3 - t_1$. If the high-frequency generators are activated for longer than $t_{13}$, $u_2$ appears and immediately switches on the acoustic signal device 14.

$IC_5$ and $IC_6$ in the delay circuit 15, each being shown in FIG. 2 as a NAND gate, are connected together to form an RS flipflop, of which the output voltage $u_3$ is set at zero or "low" when the supply voltage $U_3$ and the supply voltage $U_4$ are turned on.

If and when the voltage $u_2$ appears at the input of the delay circuit 15, it is supplied to the input of an inverter $IC_4$ over an adjustable resistance $R_6$ where it becomes effective subject to the time constant of the combination of the resistor $R_6$ and a capacitor $C_6$ to produce a delay of $\Delta t_{15} = t_4 - t_3$. A diode $D_7$ is provided for discharging by H capacitor $C_6$ practically without delay by H resistance $R_{11}$ as soon as the voltage $u_2$ drops to zero. A diode $D_8$ is provided to limit negative input voltages for $IC_4$. The output voltage $u_8$ of $IC_4$ is differentiated by a capacitor $C_8$ and the differentiated pulse $u_9 = f(t)$ is applied to the input of $IC_6$, as the result of which the RS flipflop consisting of $IC_5$ and $IC_6$ switches over and delivers the voltage $u_3$ at the output of the flipflop. The voltage $u_3$ switches off the supply current $U_1$ for the high-frequency generator 1 and $U_2$ for the high-frequency generator 6 by means of the relay 16 and 17 (in FIG. 1) practically without delay. The voltage $u_3$ is maintained until the RS flipflop is reset by a brief interruption of the supply voltage $U_3$, for example by briefly switching off the energizing AC supply line by the power switch 23 (FIG. 1) of the apparatus and then right away switching it on again, or by brief depression of a reset button or key 22.

A diode $D_{11}$ limits inverse input voltages at $IC_5$. $C_7$ and $R_7$ delay the input voltage for $IC_5$ when the high-frequency surgery apparatus is turned on, so that the RS flipflop is definitely set. $C_7$ is quickly discharged over $D_{10}$ and $R_8$ when the operating voltage $U_3$ is interrupted.

Although the invention has been described with reference to a particular illustrative example, it will be understood that modifications and variations are possible within the inventive concept.

We claim:

1. High-frequency electrosurgical unit for cutting and coagulating biological tissues, including at least one high-frequency generator capable of being individually put into and taken out of operation by control of an enabling circuit thereof including a main power on-off switch, said at least one high-frequency generator having a high-frequency transformer, said unit also comprising:

a rectifier circuit individual to said high-frequency transformer of said at least one high-frequency generator for providing a first electrical output signal ($u_1$) when and so long as said at least one high-frequency generator is in an activated state;

a first delay circuit (13), to which said first output signal ($u_1$) is provided as an input, for producing a second output signal ($u_2$) when said first output signal ($u_1$) has persisted without interruption for more than a first time interval ($t_{13}$), said first delay circuit having means for adjusting the duration of said first time interval;

means (14) connected to said first delay circuit (13) for producing an audible signal for so long as said second output signal ($u_2$) of said first delay circuit (13) persists;

a second delay circuit (15) having said second output signal ($u_2$) of said first delay circuit (13) as an input, for producing a third output signal ($u_3$) when said second output signal ($u_2$) has persisted without interruption for more than a second time interval ($t_{15}$), said second delay circuit (15) having means for adjusting the duration of said second time interval;

cut-off relay means (16,17) having a switching path interposed in said enabling circuit and connected to allow completion of said enabling circuit when said at least one one high-frequency generator is put into operation and to interrupt said enabling circuit immediately at the end of said second time interval ($t_{15}$) in response to said third output signal ($u_3$) of said second delay circuit (15), and means for restoring enablement of said at least one high-frequency generator and restarting said second delay circuit (15) after interruption of said enabling circuit by said cut-off relay means in response to turning off said main power switch and quickly thereafter turning said main power switch back on.

2. High-frequency electrosurgical unit according to claim 1, in which there are a plurality of said high-frequency generators each having an enabling circuit, a high-frequency transformer and a rectifier circuit individual thereto for producing an individual first output signal and in which said means (14) for producing an audible signal, first delay circuit (13), and second delay circuit (15) serve all said high-frequency generators, said cut-off relay means being an individual cut-off relay for each said high-frequency generator, said means for restoring enablement being effective for restoring enablement of all said high-frequency generators which were enabled prior to disablement by said cut-off relay means, said first delay circuit being connected for being made operable, in response to said first output signals of said rectifier circuits, while any of said high-frequency generators is in operation and said second delay circuit being continued in operation, after responding to said second output signal of said first delay circuit, so long as any of said high-frequency generators continues in operation.

3. High frequency electrosurgical unit according to claim 2, in which the output signals of said rectifier circuits respectively connected to said high-frequency generators are connected in common through individual output diodes (2,4) to the input of said first delay circuit at which is connected the input of a first inverter circuit (IC1) which is a component of said first delay circuit, said first delay circuit also comprising an adjustable resistance (R5) likewise connected to the input of said first delay circuit and a capacitor (C5) connected between a grounding potential and the end of said adjustable resistor not connected to said delay circuit input, a second inverter unit (IC2) with its input connected the junction of said adjustable resistor with said capacitor and its output connected to a first input of a NOR-gate (IC3), the output of said first inverter circuit being connected to a second input of said NOR-gate, the output of said NOR-gate being connected to the output of said first delay circuit (13), first and second diodes (D5, D6) being provided respectively across said adjustable resistor and said capacitor and being provided respectively for discharging said capacitor through said rectifier circuit (11, 12) when said output voltage of said rectifier circuit goes to zero and for limiting negative input voltage to said second inverter circuit (IC2).

4. High-frequency electrosurgical unit according to claim 2, in which said means for restoring enablement of said high-frequency generators comprises first and second NAND gates (IC5 and IC6) in said second delay circuit (15) connected together to constitute a RS flipflop, said second NAND-gate (IC6) having one input to which a signal ($u_9$) of said second delay circuit is provided and an output serving as the output providing said third output signal ($u_3$) of said second delay circuit, said first NAND-gate (IC5) having an input connected to a network energized by a supply voltage ($U_3$) of said electrosurgical unit energized through said main power switch (23), a second input of each of said NAND-gates being cross-connected to the output of the other of said NAND-gates, whereby brief interruption of said supply voltage ($U_3$) will terminate said third output signal ($u_3$) produced by operation of said second delay circuit (15).

5. High-frequency electrosurgical unit according to claim 4, in which a reset button switch is connected to said input of said first NAND-gate (IC5) for momentarily grounding said network connected to said supply voltage and thereby terminating said third output signal ($u_3$) produced by said second delay circuit (15).

6. High-frequency electrosurgical unit according to claim 4, in which said second delay circuit includes an adjustable resistor connected between the input of said second delay circuit and the input of an inverter circuit (IC4) and also a capacitor connected between said input of said inverter circuit and ground potential, said adjustable resistor and said capacitor being bridged by diodes in the same manner as and for the same purpose as the corresponding components of said first delay circuit, a resistor (R11) between the input of said second delay circuit and ground potential being connected for discharging said capacitor (C6) of said second delay circuit through the diode (D7) bridging said adjustable resistor when said second output voltage ($u_2$) of said first delay circuit drops to zero, the output of said inverter circuit and (IC4) being provided through a differentiating network to an input of said second NAND-gate (IC6) of said enablement restoring means.

7. High-frequency electrosurgical unit according to claim 4, in which said network energized by said supply voltage ($U_3$) and said first NAND-gate (IC5) of said enablement restoring means comprises a resistor R7 interposed between said supply voltage and an input of said first NAND-gate and a capacitor (C7) connected between said input of said first NAND-gate and ground potential, both said resistor and said capacitor connected to said input of said first NAND-gate being bridged respectively by diodes, and an additional resistor (R8) being connected between said supply voltage and ground potential, whereby the application of said supply voltage to said first NAND-gate following operation of said main power switch for turning on said high-frequency electrosurgical circuit is delayed at the input of said first NAND-gate for assuring a defined setting of said RS flipflop constituted by said first and second NAND-gates, and whereby when said supply voltage is interrupted, said capacitor (C7) connected to said first NAND-gate is discharged through said additional resistance (R8) and the said diode bridging said resistor (R7) interposed between said first NAND-gate and said supply voltage.

8. High-frequency electrosurgical unit according to claim 1, further comprising manual-reset means for restoring enablement of said at least one high-frequency generator and restarting said second delay circuit (15) after interruption of said enabling circuit by said cut-off relay means, said manual-reset means including a manually operable switch.

9. High-frequency electrosurgical unit according to claim 1, in which said means of said first and second delay circuits for respectively adjusting first and second time intervals have a range of adjustment that permits the sum of the durations of the first and second time intervals ($t_{13}+t_{15}$) to be greater than any likely normal uninterrupted activiation period of said at least one of high frequency generator.

10. High-frequency electrosurgical unit according to claim 1, in which said at least one high-frequency generator is a self-excited high-frequency generator (6) having its own output adjustment by which its output power can be set at any value within a wide range, and in which said rectifier connected to said high-frequency transformer (7) of said at least one high frequency generator (6) includes a voltage limiting diode (D4A) connected so as to limit the voltage output of said rectifier (12).

11. High-frequency electrosurgical unit according to claim 1, in which said first delay circuit includes a first inverter circuit (IC1) having its input connected directly to the input of said first delay circuit for inverting said first output signal of said rectifier, an adjustable resistance (R5) likewise connected to the input of said first delay circuit and a capacitor (C5) connected between the end of said adjustable resistor not connected to said delay circuit input and a grounding potential, a second inverter unit (IC2) connected between the junction of said adjustable resistor with said capacitor and a first input of a NOR-gate (IC3), the output of said first inverter circuit being connected to a second input of said NOR-gate, the output of said NOR-gate being connected to the output of said first delay circuit (13), first and second diodes (D5, D6) being provided respectively across said adjustable resistor and said capacitor and being provided respectively for discharging said capacitor through said rectifier circuit (11, 12) when said output voltage of said rectifier circuit disappears and for limiting negative input voltage to said second inverter circuit (IC2).

12. High-frequency electrosurgical unit according to claim 1, in which said means for restoring enablement of said at least one high-frequency generator comprises first and second NAND gates (IC5 and IC6) in said second delay circuit (15) connected together to constitute a RS flipflop, said second NAND-gate (IC6) having one input to which a signal ($u_9$) of said second delay circuit is provided and an output serving as the output providing said third output signal ($u_3$) of said second delay circuit, said first NAND-gate (IC5) having an input connected to a network energized by a supply voltage ($U_3$) of said electrosurgical unit energized through said main power switch (23), a second input of each of said NAND-gates being cross-connected to the output of the other of said NAND-gates, whereby brief interruption of said supply voltage ($U_3$) will terminate said third output signal ($u_3$) produced by operation of said second delay circuit (15).

13. High-frequency electrosurgical unit according to claim 12, in which a reset button switch is connected to said input of said first NAND-gate (IC5) for momentarily grounding said network connected to said supply voltage and thereby terminating said third output signal ($u_3$) produced by said second delay circuit (15).

14. High-frequency electrosurgical unit according to claim 12, in which said second delay circuit includes an adjustable resistor connected between the input of said second delay circuit and the input of an inverter circuit (IC4) and also a capacitor connected between said input of said inverter circuit and ground potential, said adjustable resistor and said capacitor being bridged by diodes in the same manner as and for the same purpose as the corresponding components of said first delay circuit, a resistor (R11) between the input of said second delay circuit and ground potential being connected for discharging said capacitor (C6) of said second delay circuit through the diode (D7) bridging said adjustable resistor when said second output voltage ($u_2$) of said first delay circuit drops to zero, the output of said inverter circuit and (IC4) being provided through a differentiating network to an input of said second NAND-gate (IC6) of said enablement restoring means.

15. High-frequency electrosurgical unit according to claim 12, in which said network energized by said supply voltage ($U_3$) and said first NAND-gate (IC5) of said enablement restoring means comprises a resistor R7 interposed between said supply voltage and an input of said first NAND-gate and a capacitor (C7) connected between said input of said first NAND-gate and ground potential, both said resistor and said capacitor connected to said input of said first NAND-gate being bridged respectively by diodes, and an additional resistor (R8) being connected between said supply voltage and ground potential, whereby the application of said supply voltage to said first NAND-gate following operation of said main power switch for turning on said high-frequency electrosurgical circuit is delayed at the input of said first NAND-gate for assuring a defined setting of said RS flipflop constituted by said first and second NAND-gates, and whereby when said supply voltage is interrupted, said capacitor (C7) connected to said first NAND-gate is discharged through said additional resistance (R8) and the said diode bridging said resistor (R7) interposed between said first NAND-gate and said supply voltage.

* * * * *